(12) United States Patent
Stangier

(10) Patent No.: US 9,063,163 B2
(45) Date of Patent: Jun. 23, 2015

(54) LYOPHILISED DABIGATRAN

(75) Inventor: Joachim Stangier, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 221 days.

(21) Appl. No.: 13/147,242

(22) PCT Filed: Jan. 27, 2010

(86) PCT No.: PCT/EP2010/050925
§ 371 (c)(1),
(2), (4) Date: Sep. 23, 2011

(87) PCT Pub. No.: WO2010/086329
PCT Pub. Date: Aug. 5, 2010

(65) Prior Publication Data
US 2012/0040384 A1    Feb. 16, 2012

(30) Foreign Application Priority Data
Feb. 2, 2009 (EP) .................... 09151865

(51) Int. Cl.
| *C12Q 1/56* | (2006.01) |
| *A61P 7/02* | (2006.01) |
| *G01N 33/94* | (2006.01) |
| *A61K 9/19* | (2006.01) |
| *G01N 33/96* | (2006.01) |

(52) U.S. Cl.
CPC ..... *G01N 33/94* (2013.01); *A61K 9/19* (2013.01); *G01N 33/96* (2013.01); *G01N 2496/45* (2013.01)

(58) Field of Classification Search
CPC .................. A61K 9/19; G01N 33/96
USPC ........................................... 435/13
See application file for complete search history.

(56) References Cited

U.S. PATENT DOCUMENTS

| 6,087,380 A | 7/2000 | Hauel et al. |
| 6,414,008 B1 | 7/2002 | Hauel et al. |
| 6,469,039 B1 | 10/2002 | Hauel et al. |
| 6,710,055 B2 | 3/2004 | Hauel et al. |
| 8,158,152 B2 * | 4/2012 | Palepu ............. 424/489 |
| 2003/0004181 A1 | 1/2003 | Hauel et al. |
| 2008/0200514 A1 * | 8/2008 | Clemens et al. ........ 514/338 |

FOREIGN PATENT DOCUMENTS

| CA | 2 277 949 A1 | 8/1998 |
| WO | 98/37075 A1 | 8/1998 |
| WO | 01/07921 A2 | 2/2001 |
| WO | 2006/031387 A1 | 3/2006 |

OTHER PUBLICATIONS

British J. Cl. Pharm. 2007, 64/3, pp. 192-303.*
International Search Report for PCT/EP2010/050925 mailed Mar. 29, 2010.
Stangier, Joachim, et al; Pharmacokinetics and Pharmacodynamics of the Direct Oral Thrombin Inhibitor Dabigatran in Healthy Elderly Subjects; Clinical Pharmacokinetics (2008) vol. 47, No. 1 pp. 47-58.

* cited by examiner

*Primary Examiner* — Tekchand Saidha
*Assistant Examiner* — Younus Meah
(74) *Attorney, Agent, or Firm* — Michael P. Morris; Wendy A. Petka

(57) ABSTRACT

The invention relates to a lyophilised form of dabigatran of formula (I) its use as a calibrator in the assays for the determination of pharmacodinamic effects of dabigatran etexilate as well as such assays per se. In the preparation of the lyophilised standards, dabigatran is dissolved in an aqueous acidic solution before freeze-drying.

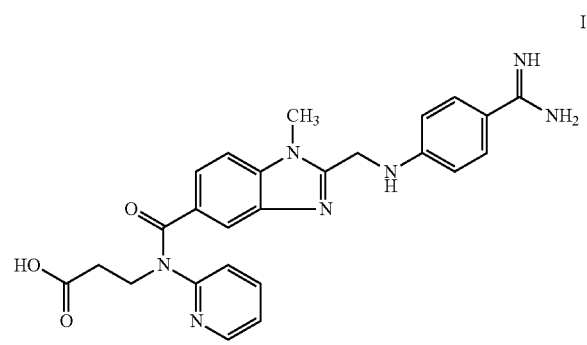

1 Claim, 1 Drawing Sheet

5
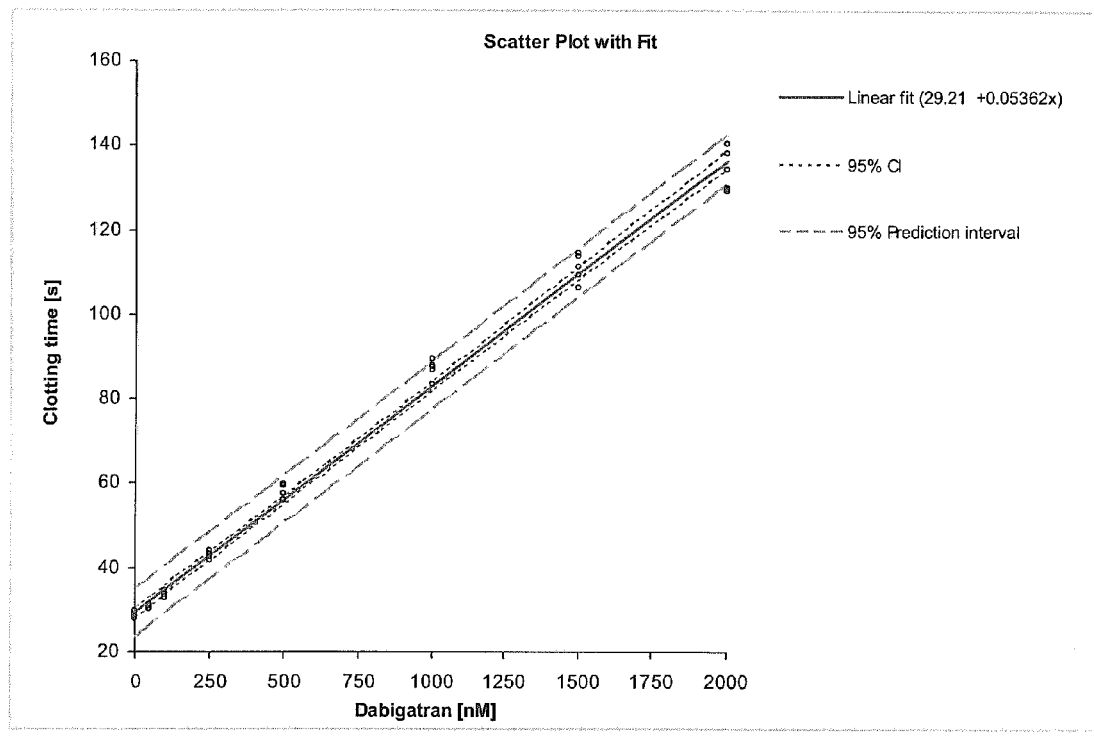
Dabigatran calibration curve (0 - 2000 nM) with linear regression line, 95 % confidence interval for the linear regression line, and the 95 % prediction interval

LYOPHILISED DABIGATRAN

This application is the national phase entry under 35 U.S.C. §371 of International Application No. PCT/EP2010/050925, filed Jan. 27, 2010, which claims priority to Eurupean Patent Application No. 09151865.4, filed Feb. 2, 2009, the contents of which are hereby incorporated by reference in their entireties.

The invention relates to a lyophilised form of dabigatran of formula I

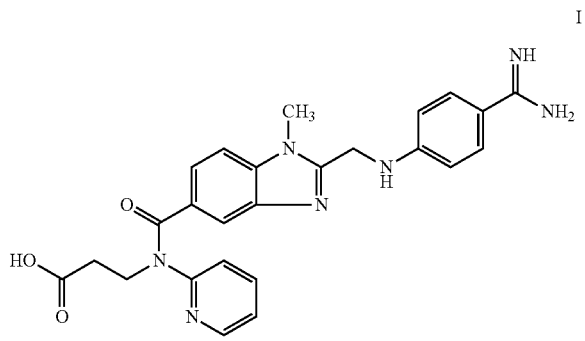 [SMILES: Cn1c(CNc2ccc(C(=N)N)cc2)nc2cc(C(=O)N(CCC(=O)O)c3ccccn3)ccc21]

I its use as a calibrator in the assays for the determination of pharmacodinamic effects of dabigatran etexilate as well as such assays per se.

BACKGROUND TO THE INVENTION

Dabigatran etexilate of formula II

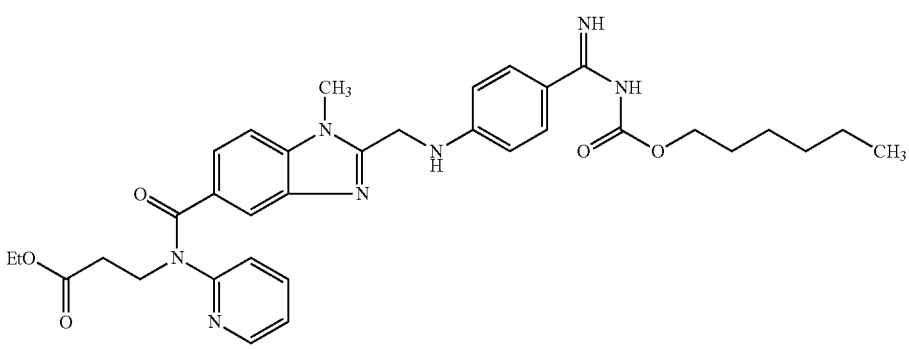

II is an oral direct thrombin inhibitor useful in the prophylaxis of thromboembolism in patients undergoing total knee or hip replacement and also suitable for the prevention of stroke, in particular in patients with atrial fibrillation. Although clinical monitoring of dabigatran etexilate is not required, a reliable laboratory method to measure the pharmacodynamic effects of dabigatran etexilate would be useful. Such a method could be used not only to monitor the kinetics of the drug activity in the body but also to adjust dosing and posology of the drug. Via such a method drug concentration in the patient's blood could be determined which could be useful to avoid overdosing. Therefore, it is the general object of the invention to provide for an assay that is useful to analyse the pharmacodynamic effects of dabigatran etexilate.

DETAILED DESCRIPTION OF THE INVENTION

The instant invention is specifically directed to a method for the quantitative determination of dabigatran in blood samples. The method comprises the determination of the clotting time that is initated by purified human thrombin.

For the determination of dabigatran concentrations the following assay principle turned out to be particularly useful. For measuring the dabigatran concentration, an aliquot of the test plasma sample is diluted with physiological saline. Coagulation is then initiated by adding a constant amount of highly purified human thrombin, in the a form. The coagulation time measured is directly proportional to the concentration of dabigatran in the tested sample.

In order to be able to determine the concentration of the active in the investigated blood sample via the strategy mentioned hereinbefore, it is necessary to have a calibration curve generated that makes a correlation of the coagulation time with the concentration of dabigatran in the sample possible.

In order to allow for the generation of such a calibration curve the assay product has to contain dabigatran standards of a defined concentration which can be shipped together with the assay product. In the instant invention the term "dabigatran standard" may also be replaced by the term "dabigatran calibrator". Such standards have to be stable and the amount of drug has to be constant when the standard is stored at −20° C. or above. The standards have to be easily applicable in the test system in order to ensure that a reliable calibration curve can be easily established.

The compound of formula I (dabigatran) is a compound that tends to crystallize in different polymorphic forms. Also the compound is hygroscopic thereby leading also to the formation of different hydrated forms. The compound is sparingly soluble.

It is the main object of the invention to provide for a form of dabigatran that can be used as a calibrator or standard for the establishment of a calibrator curve in a coagolation time assay. The instant invention proposes as a solution to this problem that dabigatran is transferred into a lyophilized form as follows.

A defined amount of dabigatran drug substance is dissolved in aqueous acid and diluted in water. This solution is used as a stock solution for the preparation of the different dabigatran calibrator samples. To human anticoagulated plasma that has been obtained from healthy volunteer donors (human pool plasma) according to methods known in the art different aliqouts of the dabigatran stock solution mentioned hereinbefore are added to lead to solutions with different dabigatran concentrations. Specified volumes of these different solutions are transferred into suitable tubes and lyophilised to complete dryness in an appropriate freeze drying device.

Therefore, the invention relates to a process for the manufacture of lyophilised dabigatran comprising the steps of dissolving dabigatran in aqueous acidic solution, adding the solution to human anticoagulated plasma and freeze-drying the thus obtained solution.

The aqueous acidic solution used for the dissolution of dabigatran is preferably characterized by a pH≤3, more preferably ≤2. The acids are preferably selected from among hydrochloric acid, hydrobroinic acid, sulfuric acid, phosphoric acid, methansulphonic acid, acetic acid, fumaric acid, citric acid, tartaric acid, and maleic acid. Of particular interest is hydrochloric acid.

The human anticoagulated plasma can be obtained according to methods known in the art. It is preferably human citrated plasma.

The lyophilized dabigatran according to the invention is easily reconstituted and, therefore, useful as a calibrator for the determination of the dabigatran concentration in blood samples. Therefore, the invention furthermore relates to lyophilised dabigatran obtainable according to the method mentioned hereinbefore.

Furthermore the invention relates to the use of the lyophilised dabigatran according to the invention as a calibrator agent in an assay. In particular the invention relates to the use of the lyophilised dabigatran according to the invention as a calibrator agent in an anticoagulation assay Stability of lyophilised dabigatran according to the invention was demonstrated for at least 24 hours at 37° C., and for at least 6 months at 4° C. and −20° C., respectively.

The invention furthermore relates to an assay for the determination of the concentration of dabigatran in a blood sample comprising the use of lyophilised dabigatran as a calibrator.

The invention furthermore relates to the aforementioned assay, characterized in that the concentration of dabigatran is determined via measurement of the coagolation time of the blood sample. The invention furthermore relates to the aforementioned assay in which coagulation is initiated by adding a constant amount of highly purified human thrombin in the α form.

In another object of the invention an assay kit is provided that contains the dabigatran calibrator according to the invention. Accordingly, the invention furthermore relates to an assay for the determination of the concentration of dabigatran in a blood sample comprising the use of lyophilised dabigatran obtained according to the method mentioned hereinbefore.

The invention furthermore relates to a kit consisting of an assay for the determination of the concentration of dabigatran in a blood sample together with lyophilised dabigatran obtained according to the method mentioned hereinbefore.

The invention furthermore relates to the aforementioned kit wherein the assay for the determination of the concentration of dabigatran in a blood sample comprises a reagent 1 which is human anticoagulated plasma and a reagent 2 which comprises highly purified human thrombin in the α form. In another preferred embodiment the kit contains reagent 1 and reagent 2 in lyophilised form.

With lypoghilised dabigatran samples of defined concentrations a quality control system is available. Quality control sample coagulation time measurement and subsequent determination of the corresponding dabigatran concentration using the calibration curve allows for the determination of assay accuracy. Assay accuracy is assessed by comparison of the known target concentration of the dabigatran quality control sample and the calculated concentration of this quality control sample using the coagulation time and calibration curve.

Therefore, in another embodiment the invention relates to the use of the lyophilised dabigatran according to the invention to determine the accuracy of an assay. In particular the invention relates to the use of the lyophilised dabigatran according to the invention to determine accuracy of an anticoagulation assay.

The Examples that follow serve to illustrate the present invention in more detail.

Materials and Methods

The chronometric coagulation assays were performed with two Behnk CL4 ball coagulometers (Behnk Elektronik, Germany). This equipment was used in line to the operating instructions of the manufacturer.

The Thrombin Inhibitor assay kit used in the assay according to the invention is commercially available. It is manufactured by HYPHEN BioMed, France and obtainable on the market as Hemoclot® Thrombin Inhibitors assay. The kit components that are used in the instant invention are the following 2 reagents:

Reagent 1: normal pooled citrated plasma, lyophilised
Reagent 2: highly purified human calcium thrombin (in alpha-form) stabilized with additives and lyophilised.

The performance of the coagulation test with dabigatran plasma samples was evaluated with the analytical method evaluation programme 'Analyse-it' for Excel, Version 2.09, Analyse-it Software, Ltd. PO Box 103, Leeds LS27 7WZ England, United Kingdom.

A) Preparation of Lyophilised Dabigatran Calibrators 5.55 mg Dabigatran of formula I is dissolved in 200 µL 1M HCl and diluted in ultra pur water water to give a final volume of 50 mL. This stock solution of 111 µg/mL dabiagatran is stored at 4° C. Human citrated plasma from healthy volunteer donors (human pool plasma) is used for the preparation of dabigatran calibrators. Aliqouts of the dabigatran stock solution are diluted in human citrated pool plasma to lead to solutions with the different final dabigatran concentrations 100, 500, 1500 and 2000 nM dabigatran.

Aliqouts of 500 µL volume of the human pool plasma with 100, 500, 1500 or 2000 nM dabigatran are transferred into polypropylene tubes and lyophilised using a Christ Alpha RVC, Type CMC-2 vacuum centrifuge to complete dryness for approximately 8 hours (pressure: 3 mbar). Lyophilised dabigatran calibrators are stored at .−20° C.

B) Preparation of Standards (Calibration Curve)

Add to each vial of the according to step A obtained dabigatran calibrators of 0 (blank), 100, 500, 1500 and 2000 nM dabigatran 0.5 mL ultra pure water. Mix gently. Incubate for 15 min at ambient temperature.

Calibrator plasma must be diluted 1:8 e.g. 100 µL standard and 700 µL phys. NaCl Pipette 50 µL of calibrator sample into the coagulometer cuvettes (duplicate determination) Measure each calibrator as described in 'measurement procedure'.

C) Preparation of Reagents:

Calculate the necessary volume of reagents for the daily amount of samples. Solve each vial of Reagent 1 and 2 in 1 mL ultra pure water; mix gently, incubate for 15 min at ambient temperature.

stability of prepared reagents:

| Reagent 1: | +18-+25° C. | 24 h |
| | +2-+8° C. | 48 h |
| | −20° C. | 2 month |

| -continued | | |
|---|---|---|
| Reagent 2 | +18-+25° C. | 24 h |
| | +2-+8° C. | 48 h |
| | −20° C. | 2 month |

D) Plasma Sample Collection and Preparation:

Collect blood sample on 0.109 M trisodium citrate anticoagulant (ratio 9:1 blood/citrate). Decant plasma supernatant following a 20 Min centrifugation at 2.5 g.

| stability of plasma: | +18-+25° C. | 8 h |
|---|---|---|
| | +2-+8° C. | 24 h |
| | ≤−20° C. | up to 6 months |

Thaw samples at +37° C. for maximal 45 min. Keep thawed samples at ambient temperature. Sample plasma must be diluted 1:8 e.g. 1004 sample and 7004 phys. NaCl E) Measurement Procedure The following measurement procedure is conducted first with the calibrator samples prepared according to step B. After preparation of the calibration curve, the plasma samples prepared according to step D are measured accordingly.

Mix samples (calibrator or plasma) by gentle agitation. Transfer 50 µL plasma sample each (obtained according to step B or D) into 2 cuvettes (each sample is measured in duplicate). Pipette 100 µL Reagent 1 (preincubated at 37° C.) into cuvette. At the same time, start a 1 min incubation period by activating a timer. By the end of the incubation time add 100 µL Reagent 2 (preincubated at 37° C.) to the cuvette. A stopwatch is started. The time until the ball's rotation in the Behnk CL4 ball coagulometer stops is measured (clotting time [sec]). The instrument's software calculates the mean clotting time [sec] of the duplicate measurement. The result of both determinations and the mean clotting time is documented on paper print F) Generation of Calibration Curve:

The coagulation times obtained by measuring the calibrator samples with 0 (blank sample), 100, 500, 1500 and 2000 nM (wider concentration range and additional concentrations, e.g. 250 nM are possible) are plotted versus the dabigatran calibrator concentration in a scatter plot using a spreadsheet program (MS Excel or the like). A calibration curve is established by simple linear regression analysis.

By way of example a calibration curve based on dabigatran standards with concentrations of 50, 100, 250, 500, 1000, 1500, and 2000 nM respectively is depicted in FIG. 1.

By determination of the coagulation time, the corresponding dabigatran concentration in a plasma sample can be determined directly from the calibration line.

With lypoghilised dabigatran samples of defined concentrations, e.g. 100, 500 and 1500 nM, a quality control system is available. Quality control sample coagulation time measurement and subsequent determination of the corresponding dabigatran concentration using the calibration curve allows for the determination of assay accuracy. Assay accuracy is assessed by comparison of the known target concentration of the dabigatran quality control sample and the calculated concentration of this quality control sample using the coagulation time and calibration curve.

The invention claimed is:

1. A method of producing a lyophilized composition comprising dabigatran of formula I

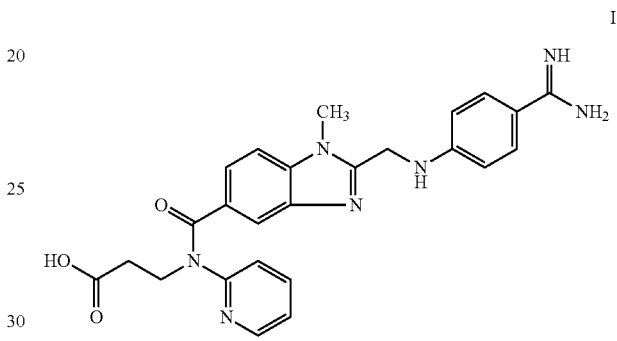

and human anticoagulated plasma for use as a calibrator agent or calibrator agent in an anticoagulant assay comprising the steps of:
 (1) dissolving dabigatran in 1M HCl and diluting with purified water to make a dabigatran stock solution,
 (2) diluting aliquots of dabigatran stock solution with human anticoagulated plasma to provide final solutions having different nanomolar concentrations of dabigatran, wherein the human anticoagulated plasma is human citrated plasma or EDTA-anticoagulated plasma, and
 (3) freeze-drying aliquots of the thus obtained final solutions to be used as lyophilized calibrator agents or lyophilized calibrator agents in an anticoagulant assay, optionally storing lyophilized calibrators at −20° C.

* * * * *